United States Patent [19]

Costantini et al.

[11] Patent Number: 4,877,903

[45] Date of Patent: Oct. 31, 1989

[54] CYCLOHEXANOL/CYCLOHEXANONE MIXTURES PRODUCED FROM CYCLOHEXANE

[75] Inventors: Michel Costantini, Lyons; Francoise Igersheim, Villeurbanner, both of France

[73] Assignee: Rhone-Poulenc Chimie, Courbevoie, France

[21] Appl. No.: 271,346

[22] Filed: Nov. 14, 1988

Related U.S. Application Data

[63] Continuation of Ser. No. 106,773, Oct. 13, 1987, abandoned.

[30] Foreign Application Priority Data

Oct. 10, 1986 [FR] France .................................. 86 14282

[51] Int. Cl.[4] ............................................. C07C 45/33
[52] U.S. Cl. ................................... 568/342; 568/836; 568/360
[58] Field of Search ........................ 568/360, 342, 836

[56] References Cited

U.S. PATENT DOCUMENTS

| | | | |
|---|---|---|---|
| 3,923,895 | 12/1975 | Costantini et al. | 568/342 |
| 4,326,084 | 4/1982 | Druliner et al. | 568/836 |
| 4,341,967 | 7/1982 | Zelonka | 568/570 |
| 4,465,861 | 8/1984 | Hermolin | 568/342 |
| 4,482,746 | 11/1984 | Hermolin | 568/342 |
| 4,508,923 | 4/1985 | Taylor et al. | 568/342 |

*Primary Examiner*—James H. Reamer
*Attorney, Agent, or Firm*—Burns, Doane, Swecker & Mathis

[57] ABSTRACT

Mixtures containing cyclohexanol and cyclohexanone are produced by oxidizing cyclohexane with air, and then decomposing the cyclohexyl hydroperoxide in such reaction mixture, in the presence of the cyclohexane, to form cyclohexanol and cyclohexanone, such oxidation and/or decomposition being carried out in the presence of a manganese source, a Brönsted acid and a pyridine ligand.

16 Claims, No Drawings

CYCLOHEXANOL/CYCLOHEXANONE MIXTURES PRODUCED FROM CYCLOHEXANE

This application is a continuation of application Ser. No. 106,773, filed Oct. 13, 1987 abandoned.

BACKGROUND OF THE INVENTION

1. Field of the Invention

The present invention relates to the preparation of a mixture containing cyclohexanol and cyclohexanone from cyclohexane.

More especially, this invention relates to a process in which cyclohexane is oxidized in the presence of air to form a mixture containing cyclohexyl hydroperoxide, hereinafter referred to as CHHPO, such hydroperoxide then being decomposed. The principal products formed during the decomposition are cyclohexanol (OL) and cyclohexanone (ONE). These compounds are converted by oxidation into adipic acid, one of the main starting materials in the production of polyamides. Cyclohexanone is also an intermediate for producing caprolactam, a compound used in the manufacture of certain polyamides.

2. Description of the Prior Art

D. Mansuy and his co-workers have described, in *Angew. Chem., Int. Ed. Engl.*, 19, No. 11, pages 909–910 (1980), the oxidation of cyclohexane with cumyl hydroperoxide, in the presence of the complex:

$$Mn^{III}(TPP)Cl,$$

wherein TPP is tetraphenylporphyrin.

However, the yields remain low, and the catalyst is expensive and sensitive to oxygen. Additionally, it is essential to conduct the reaction in the presence of a solvent.

Although French Pat. No. 1,263,449 describes the decomposition of cyclohexyl hydroperoxide in a mixture resulting from the oxidation of cyclohexane, prior to the separation of the latter, in the presence of a manganese and copper combination which can be dispersed in the reaction mixture, this is a total decomposition. However, the cyclohexane is not oxidized.

Moreover, an improved process for the oxidation of cyclohexane to form a reaction mixture containing CHHPO and for the decomposition of such hydroperoxide in the presence of cyclohexane (starting material) to form a mixture containing cyclohexanol and cyclohexanone is described in published European Patent Application No. EP-A-0,027,937. This improved process features the use of a complex of a transition metal and compounds of the 1,3-bis(pyridylimino)isoinodoline group as catalyst in the oxidation and/or decomposition stage.

An important aspect of this process resides in the participation of the cyclohexane, namely, a higher conversion of said cyclohexane into "useful" oxidation products than that which would normally be observed during the decomposition of CHHPO alone.

However, this process has two major disadvantages: firstly, the use of ligands which are very expensive and/or difficult to prepare and secondly, the sensitivity of such ligands to oxidizing agents.

SUMMARY OF THE INVENTION

Accordingly, a major object of the present invention is the provision of an improved process for the oxidation of cyclohexane which ameliorates those disadvantages and drawbacks to date characterizing the state of this art.

Briefly, the present invention features an improved process for the production of a mixture of cyclohexanol and cyclohexanone, in which the cyclohexane is oxidized by air to produce a mixture containing cyclohexyl hydroperoxide, and further wherein the cyclohexyl hydroperoxide is decomposed in the presence of cyclohexane to form cyclohexanol and cyclohexanone, said improvement comprising:

(1) the oxidation of cyclohexane in air at a temperature of from 80° C. to 160° C., in the presence of a catalytically effective amount of (i) manganese or a manganese compound, (ii) a Brönsted acid having a $pK_a$ greater than or equal to 0.7 and (iii) a pyridine ligand having any one of formulae (I) to (III) below; and/or (2) the decomposition of cyclohexyl hydroperoxide by contacting a reaction mixture containing cyclohexane and approximately 0.1 to 10% by weight of cyclohexyl hydroperoxide with a pyridine ligand having any one of the formulae (I) to (III) below, in the presence of a catalytically effective amount of (i) manganese or a manganese compound, (ii) a Brönsted acid having a $pK_a$ greater than or equal to 0.7, at a temperature of from 60° C. to 160° C., and, where appropriate, in the presence of (iv) molecular oxygen:

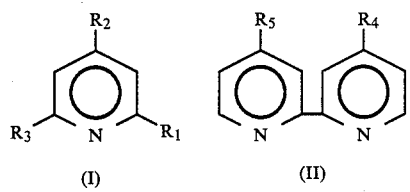

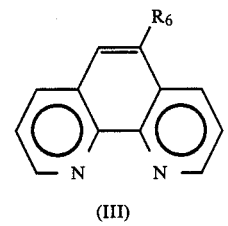

wherein:

$R_1$, $R_2$ and $R_3$, which may be identical or different, are each a hydrogen atom, a straight or branched chain alkyl radical containing up to 4 carbon atoms, and being devoid of substituents likely to interfere with the principal reaction, or a carboxyl group;

$R_4$ and $R_5$, which may be identical or different, have the definitions given above for $R_1$, $R_2$ and $R_3$, with the proviso that, when $R_4$ or $R_5$ represents a carboxyl group, the other symbol represents hydrogen or an alkyl radical; and $R_6$ is a hydrogen atom, a straight or branched chain alkyl radical containing up to 4 carbon atoms, also devoid of substituents likely to interfere with the principal reaction, or a nitro group.

DETAILED DESCRIPTION OF THE PREFERRED EMBODIMENTS OF THE INVENTION

More particularly according to the present invention, the subject process thus requires the presence of a catalytically effective amount of manganese or of a manganese compound.

By "catalytically effective amount" is intended a concentration sufficient to provide an industrially acceptable reaction rate, which rate also depends on other reaction conditions, without, at the same time, complicating the operations of recycling and/or purification of the desired products.

In general, the manganese concentration in the liquid reaction medium is at least 1 millimole per liter (mmol/1). No advantage is observed in exceeding a concentration on the order of 25 mmol/1.

Finely divided manganese metal and, more generally, any manganese compound, are well suited for carrying out the present process. Compounds of manganese (II), as well as of manganese (III), may be used for this purpose. Exemplary of compounds which are well suited for carrying out the process of the invention, representative are: manganous acetate, manganic acetate and, more typically, manganese (II) or (III) carboxylates, manganous sulfate, nitrate and carbonate and manganese (III) acetylacetonate.

The use of manganese acetates or of manganese (III) acetylacetonate is preferred.

Carrying out the present process requires the presence of a pyridine ligand corresponding to any one of the formulae (I) to (III) above.

Insofar as the ligands of formula (I) are concerned, those in which the symbols $R_1$ to $R_3$ independently represent hydrogen, a methyl radical or a carboxyl group, are more particularly preferred. Exemplary of such ligands, representative are: pyridine, 2-picoline, 4-picoline, 2,6lutidine, 2,4,6-collidine (or 2,4,6-trimethylpyridine), 2-carboxypyridine and 4-carboxypyridine.

Insofar as the ligands of formula (II) are concerned, those in which the symbols $R_4$ and $R_5$ in formula (II) independently represent a hydrogen atom or a methyl radical, or when $R_4$ (or $R_5$) represents a carboxyl group, $R_5$ (or $R_4$) represents a hydrogen atom or a carboxyl group, are advantageously employed.

Exemplary of such ligands, representative are 2,2-bipyridine (or 2,2'-bipyridyl), 4,4'-dimethyl-2,2'-bipyridine and 4,4'-dicarboxy-2,2'-bipyridine.

Finally, the more particularly preferred ligands of formula (III) correspond to those in which the symbol $R_6$ represents a hydrogen atom or a methyl radical and are designated 1,10-phenanthroline or 5-methyl-1,10-phenanthroline, respectively.

2,2'-Bipyridine and 4,4'-dicarboxy-2,2'-bipyridine are particularly preferred.

In general, the amount of pyridine ligand is such that the atomic ratio N/Mn ranges from 1 to 10 and preferably from 3 to 5. Satisfactory results are obtained when this ratio is on the order of 4.

As heretofore mentioned, the present invention requires the presence of a Brönsted acid, the $pK_a$ of which, as determined at 25° C., is higher than 0.7. All or a portion of this acid may, of course, originate from the pyridine ligand bearing one or two carboxyl groups.

Exemplary acids which are within the scope of this invention, representative are: benzoic acid, saturated aliphatic monocarboxylic acids containing 1 to 12 carbon atoms in the main chain and which may contain at most three substituents selected from among $C_1$-$C_4$ alkyl radicals and chlorine and bromine atoms.

Exemplary of acids (not originating from pyridine ligands) suitable for carrying out the process of the invention, representative are: acetic acid, benzoic acid, monochloroacetic acid, hexanoic acid and dichloroacetic acid.

It will be appreciated that hexanoic or caproic acid, a coproduct of the oxidation of cyclohexane, is more particularly well suited.

Typically, the amount of acid employed is such that the atomic ratio $H^+/Mn$ ranges from 2 to 20 and preferably from 8 to 15.

Although it is possible according to the present invention to carry out the oxidation and the decomposition stages in a single operation, or in two separate operations, in the presence of the same catalytic system comprising, as mentioned above, manganese, a pyridine ligand and a Brönsted acid having a $pK_a$ greater than or equal to 0.7, it is preferred to carry out the process in two separate operations. In such case, the oxidation can be carried out in the absence of a catalyst, or in the presence of a different catalytic system, such as, for example, that described in U.S. Pat. No. 3,923,895.

Indeed, the participation of the cyclohexane in the cyclohexyl hydroperoxide decomposition stage can be increased when such decomposition is carried out in a separate operation.

As regards the oxidation, the conditions thereof will advantageously be as follows:

The temperature will range from 80° C. to 160° C. and the pressure required to maintain the cyclohexane in the liquid phase will vary, depending on the temperature selected from atmospheric pressure to 20 bars.

The decomposition reaction is carried out in the liquid phase, the concentration of cyclohexyl hydroperoxide ranging from 0.1 to 10% by weight. This concentration advantageously ranges from 0.5 to 8%.

Various solvents can be used, such as alkanes, in particular hexane, heptane and isooctane; cycloalkanes, exemplary of which being cyclohexane and cyclooctane; and aromatic hydrocarbons, such as benzene, toluene and xylene and mixtures thereof.

However, it should be noted that, as cyclohexyl hydroperoxide is produced in the form of a solution in cyclohexane by oxidation, as mentioned above, the decomposition reaction is advantageously carried out using a solution originating from the oxidation of cyclohexane, in which the concentration of the cyclohexyl hydroperoxide is within the limits noted above. This solution may be employed as is, or after the removal of certain constituents in a manner known per se. It is also possible to employ a solution of cyclohexyl hydroperoxide in substantially pure cyclohexane.

Although the decomposition of cyclohexyl hydroperoxide may be carried out in the absence of oxygen or of air, the presence of oxygen or of air is advantageous, insofar as it increases the yield of cyclohexanol/cyclohexanone without, however, deleteriously affecting the decomposition of hydroperoxide.

Nevertheless, for safety reasons, it will be advisable to ensure that the quantity of oxygen in the gaseous phase or in the reactor atmosphere remains below 5% by volume.

The temperature generally ranges from 60° C. to 160° C. Beyond 120° C., a thermal decomposition occurs, which can be undesirable.

Atmospheric pressure or a pressure greater than atmospheric pressure will be sufficient to maintain the cyclohexane in the liquid phase.

The reaction period (or residence time) generally ranges from 10 minutes to 5 hours and may be adjusted, taking into account the production objectives, the quantity of the various constituents of the catalytic system employed and other reaction parameters.

When the reaction is complete, the products may be recovered by any suitable means, for example, by distillation.

In order to further illustrate the present invention and the advantages thereof, the following specific examples are given, it being understood that same are intended only as illustrative and in nowise limitative.

In said examples to follow, these conventions are employed:

(a) DC (CHHPO) denotes the degree of conversion of the cyclohexyl hydroperoxide employed; and (b) CY (OLONE) denotes the apparent yield of cyclohexanone and cyclohexanol, i.e., the ratio of the number of moles of cyclohexanone and of cyclohexanol formed to the number of moles of cyclohexyl hydroperoxide converted.

A yield greater than 100% indicates that a fraction of the products in question emanates from the oxidation of cyclohexane.

EXAMPLE 1

The following materials were charged, under an inert atmosphere, into a reactor equipped with a central stirrer and a condenser:

(i) 84 g (1 mole) of cyclohexane;
(ii) 90 mg (0.25 mmol) of manganese acetylacetonate [Mn(acac)$_3$];
(iii) 118 mg (0.75 mmol) of 2,2'-bipyridine; and
(iv) 178 mg (1.53 mmol) of caproic acid (pK$_a$=4.4).

The mixture was heated to 60° C. and when this temperature was reached, the following were added as quickly as possible:

(v) 6 g of 97% cyclohexyl hydroperoxide.

The stirring was maintained until the peroxide oxygen content was zero or stable (which required approximately 6 hours in the present example). This time period is designated "reaction time" hereinafter. The mixture was cooled and the residual peroxide oxygen was reduced using triphenylphosphine. The mixture was then analyzed by gas chromatography.

It contained:

| (1) Residual hydroperoxide | 432.7 mg, which amounted to 3.7 mmol; |
| (2) Cyclohexanol | 3,680 mg, which amounted to 36.8 mmol; |
| (3) Cyclohexanone | 2,018 mg, which amounted to 20.6 mmol. |

This corresponded to:

| (a) DC (CHHPO) | 92.5% |
| (b) CY (OLONE) | 115.8% |

CONTROL TEST (a)

The procedure of Example 1 was repeated, but the caproic acid charge was omitted.

The reaction time was 5 hours and the results were as follows:

| (a) DC (CHHPO) | 56% |
| (b) CY (OLONE) | 106% |

CONTROL TEST (b)

The procedure of Example 1 was repeated, but the bipyridine charge was omitted.

The reaction time was 5 hours and the results were as follows:

| (a) DC (CHHPO) | 65% |
| (b) CY (OLONE) | 86% |

The particular conditions and the results obtained in Example 1 and control tests (a) and (b) are reported in Table I below:

TABLE I

| Reference | Acid present | Bipyridine present | Time in hours | DC (%) (CHHPO) | CY (%) (OLONE) |
|---|---|---|---|---|---|
| Ex. 1 | yes | yes | 6 | 92.5 | 115.8 |
| a | no | yes | 5 | 56 | 106.0 |
| b | yes | no | 5 | 65 | 86.0 |

The control tests (a) and (b) demonstrated that, in the absence of acid or of bipyridine, the degree of conversion remained low and the OLONE selectivity was insufficient.

EXAMPLE 2

The procedure of Example 1 was repeated but the bipyridine was replaced by:

(iii) 138 mg (which amounted to 0.75 mmol) of 4,4'-dimethyl-2,2'-bipyridine.

The results obtained after 4 hours of reaction were as follows:

| (a) DC (CHHPO) | 98.4% |
| (b) CY (OLONE) | 116.5% |

EXAMPLE 3

The procedure of Example 1 was repeated, but the bipyridine and the caproic acid were replaced by:

(iii) 183 mg (which amounted to 0.75 mmol) of 4,4'-dicarboxy-2,2'-bipyridine.

The results obtained after 5 hours of reaction were as follows:

| (a) DC (CHHPO) | 77.5% |
| (b) CY (OLONE) | 115.5% |

EXAMPLE 4

The procedure of Example 1 was repeated, but charging:

(iv) 300 mg (which amounted to 2.5 mmol) of caproic acid.

The results obtained after 3 hr, 30 min, of reaction were as follows:

| (a) DC (CHHPO) | 94% |
|---|---|
| (b) CY (OLONE) | 120% |

EXAMPLE 5

The procedure of Example 1 was repeated, but charging an equivalent amount of manganese in the form of $Mn(NO_3)_2$.

The results obtained after 5 hours of reaction were as follows:

| (a) DC (CHHPO) | 100% |
|---|---|
| (b) CY (OLONE) | 110% |

EXAMPLES 6 to 8

A series of tests was carried out using the apparatus and according to the procedure of Example 1, the charge containing, in each test:
(i) 84 g (1 mole) of cyclohexane;
(ii) 90 mg (0.25 mmol) of manganese acetyl acetonate [$Mn(acac)_3$];
(iii) 140 mg (0.75 mmol) of 4,4'-dimethyl-2,2'-bipyridine; and
(iv) 1.25 mmol of acid, the nature of which is given below.

The temperature was 60° C.

The particular conditions and the results obtained in each test are reported in Table II below.

TABLE 11

| Example | Acid Nature | $pK_a$ | Time in hours | DC (%) (CHHPO) | CY (%) (OLONE) |
|---|---|---|---|---|---|
| 6 | $CH_2ClCOOH$ | 2.85 | 3.5 | 100 | 112.5 |
| 7 | $CHCl_2COOH$ | 1.5 | 1 | 100 | 107 |
| 8 | $CCl_3COOH$ | 0.7 | 6 | 89 | 118 |

EXAMPLE 9

The following materials were charged into an apparatus similar to that described in Example 1:
(i) 84 g (1 mole) of cyclohexane;
(ii) 90 mg (0.25 mmol) of manganese acetylacetonate [$Mn(acac)_3$];
(iii) 137 mg (0.75 mmol) of 4,4'-dimethyl-2,2'-bipyridine; and
(iv) 178 mg (1.5 mmol) of caproic acid.

The mixture was then heated at 80° C. under nitrogen and 6 g of CHHPO were added thereto. The solution was then placed under cyclohexane-saturated air at a flow rate of 10 l/hr (determined under normal conditions of temperature and pressure).

The results obtained after 5 hours of reaction were as follows:

| (a) DC (CHHPO) | 93% |
|---|---|
| (b) CY (OLONE) | 135% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a cyclohexanol/cyclohexanone admixture, comprising oxidizing cyclohexane in air, at a temperature of from about 80° C. to 160° C., and concomitantly decomposing cyclohexyl hydroperoxide thus formed, in the presence of a catalytically effective amount of (i) manganese or compound thereof, (ii) a Brönsted acid having a $pK_a$ of at least 0.7, and (iii) a pyridine ligand.

2. A process for the preparation of a cyclohexanol/cyclohexanone admixture, comprising contacting, at a temperature of from about 60° C. to 160° C., a reaction mixture containing cyclohexane and from about 0.1 to 10% by weight of cyclohexyl hydroperoxide with a pyridine ligand in the presence of a catalytically effective amount of (i) manganese or compound thereof, (ii) a Brönsted acid having a $pK_a$ of at least 0.7, and, optionally, (iv) molecular oxygen.

3. The process as defined by claims 1 or 2, said pyridine ligand having any one of the formulae (I) to (III):

(I)

(II)

(III)

wherein $R_1$, $R_2$ and $R_3$, which may be identical or different, are each a hydrogen atom, an inert straight or branched chain alkyl radical containing up to 4 carbon atoms, or a carboxyl group; $R_4$ and $R_5$, which may be identical or different, have the definitions given above for $R_1$, $R_2$ and $R_3$, with the proviso that, when one of $R_4$ or $R_5$ is a carboxyl group, the other is a hydrogen atom or an alkyl radical; and $R_6$ is a hydrogen atom, an inert straight or branched chain alkyl radical containing up to 4 carbon atoms, or a nitro group.

4. The process as defined by claim 2, carried out in the presence of molecular oxygen.

5. The process as defined by claim 3, wherein the manganese concentration in the reaction medium ranges from 1 to 25 mmol/l.

6. The process as defined by claim 3, wherein the amount of pyridine ligand is such that the atomic ratio N:Mn ranges from 1:1 to 10:1.

7. The process as defined by claim 3, wherein the amount of Brönsted acid is such that the atomic ratio $H^+$:Mn ranges from 2:1 to 20:1.

8. The process as defined by claim 3, wherein the pyridine ligand $R_1$, $R_2$ and $R_3$, which may be identical or different, are each hydrogen, methyl, or carboxyl;

$R_4$ and $R_5$ are each hydrogen or methyl, or when $R_4$ (or $R_5$) is carboxyl, the other is hydrogen or carboxyl; and $R_6$ is hydrogen or methyl.

9. The process as defined by claim 8, wherein the pyridine ligand has the formula (II).

10. The process as defined by claim 9, wherein the pyridine ligand is 2,2'-bipyridine or 4,4'-dicarboxy-2,2'-bipyridine.

11. The process as defined by claim 3, wherein the Brönsted acid comprises the pyridine ligand, said pyridine ligand bearing one or two carboxyl substituents.

12. The process as defined by claim 3, said Brönsted acid comprising benzoic acid, a saturated aliphatic monocarboxylic acid containing from 1 to 12 carbon atoms, or a substituted such monocarboxylic acid bearing up to three $C_1$-$C_4$ alkyl radical, chlorine atom or bromine atom substituents.

13. The process as defined by claim 12, said Brönsted acid comprising caproic acid 14. The process as defined by claim 3, wherein the manganese (i) comprises a manganese (II) or manganese (III) compound.

15. The process as defined by claim 14, wherein the manganese (i) comprises an acetate.

16. The process as defined by claim 14, wherein the manganese (i) comprises manganese (III) acetylacetonate.

* * * * *